(12) United States Patent
Chen

(10) Patent No.: US 6,680,393 B1
(45) Date of Patent: Jan. 20, 2004

(54) WHITE WAX AND METHOD OF MANUFACTURE

(76) Inventor: Tsai-Kui Chen, 1E, No. 26, Zhili Rd., Tamsui City, Taipei (TW)

( * ) Notice: Subject to any disclaimer, the term of this patent is extended or adjusted under 35 U.S.C. 154(b) by 14 days.

(21) Appl. No.: 10/191,211

(22) Filed: Jul. 9, 2002

(51) Int. Cl.[7] .................................................. C07C 1/00
(52) U.S. Cl. .............................................. 554/19; 554/8
(58) Field of Search .................................. 554/8, 19

*Primary Examiner*—Deborah D. Carr
(74) *Attorney, Agent, or Firm*—Brown & Michaels, PC

(57) ABSTRACT

This invention relates to a kind of white wax and its manufacturing method, particularly the white wax extracted from animal fat and sebum as a nontoxic, non-hazardous product of superb moistening that enhances skin's elasticity while keeping skin from cracking. The white wax in reference is made of animal fat and sebum, duly crushed after pre-treatment of high-temperature sterilization and deodorization and removal of impurities, allowing the fat and sebum to mix. The mixed raw material is heated after undergoing rapid refrigeration before being minced into sticky colloid when cooled and when squeezed and screened, the sticky discharges gummy matter which, when mixed and neutralized with emulsifying agent, allowing the gummy matter transform from greasy substance into watery white wax.

8 Claims, 1 Drawing Sheet

WHITE WAX AND METHOD OF MANUFACTURE

BACKGROUND OF THE INVENTION

Field of the Invention

The invention pertains to the field of waxes and the manufacture thereof. More particularly, the invention pertains to an absorptive, non-toxic and non-harmful white wax of multiple ingredients, and a method for manufacturing same.

SUMMARY OF THE INVENTION

This invention relates to a kind of white wax and its manufacturing method, particularly the white wax extracted from animal fat and sebum as a nontoxic, non-hazardous product of superb moistening that enhances skin's elasticity while keeping skin from cracking. The white wax in reference is made of animal fat and sebum, duly crushed after pre-treatment of high-temperature sterilization and deodorization and removal of impurities, allowing the fat and sebum to mix. The mixed raw material is heated after undergoing rapid refrigeration before being minced into sticky colloid when cooled and when squeezed and screened, the sticky discharges gummy matter which, when mixed and neutralized with emulsifying agent, allowing the gummy matter transform from greasy substance into watery white wax.

DETAILED DESCRIPTION OF THE INVENTION

Figure 1:
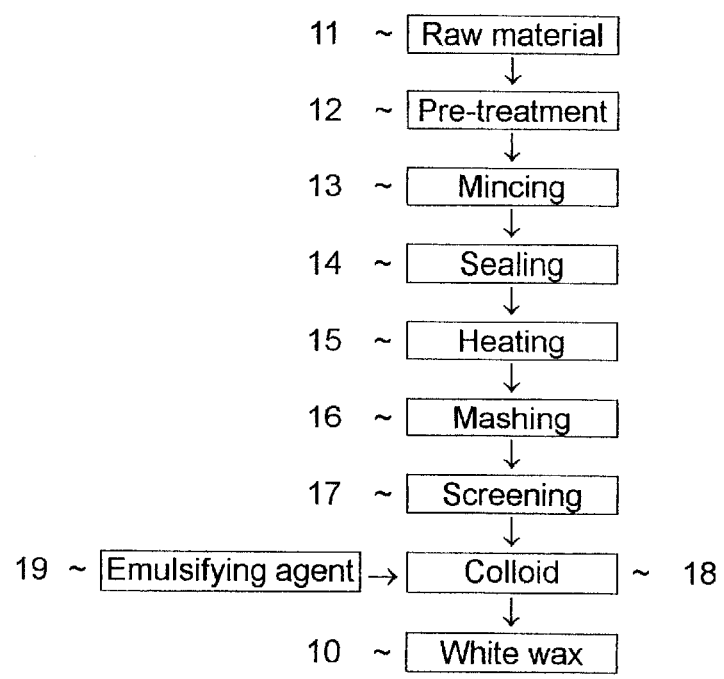
FIG. 1 shows the manufacturing process of the present invention.

This invention relates to a kind of white wax and its manufacturing method; particularly, an absorptive, non-toxic and non-harmful white wax of multiple ingredients and the manufacturing method.

Nowadays people live in dusty and noisy cities are vulnerable to skin diseases triggered by smog and skin tend to lose colloid because of persisting wind, sunshine and rainfall that leave the skin with cracks and wrinkles. While people become more and more concerned about their appearance, we are seeing a wide variety of cleansing, skin-care and cosmetic products. The cleansing products aim to remove dirt and aging corneous among other dirt while the skin-care products are to make the skin more elastic by reducing the loss of gummy matters during the aging process that would leave the skin with cracks and wrinkles. The cosmetic products are mainly to strengthen the facial profile by giving it a different touch and style.

To enhance the stickiness and stability of said cleansing items, skin-care products and cosmetic products; white wax is an essential substance, which used to be made of petroleum being diluted with nutrients for people when ready. The old item may have made cleansing items, skin-care products and cosmetic products more sticky and stable, the white wax extracted from petroleum is hard to absorb by the skin and the chemicals contained in the compound nutrients make the skin allergic and uncomfortable.

The invention in reference provides a kind of white wax and the manufacturing method, which is made of animal fat and sebum, duly crushed after pre-treatment of high-temperature sterilization and deodorization and removal of impurities, allowing the fat and sebum to mix. The mixed raw material is heated after undergoing rapid refrigeration before being minced into sticky colloid when cooled and when squeezed and screened, the sticky discharges gummy matter which, when mixed and neutralized with emulsifying agent, allowing the gummy matter transform from greasy substance into watery white wax.

The main purpose of this invention is to provide a kind of non-toxic and non-harmful white wax and the manufacturing method, which is made of animal fat and sebum and contains a wide variety of nutrients itself without adding compound nutrients. Further, the white wax tends to be absorptive and moistening.

As shown in FIG. 1, the manufacturing process of white wax (10) is as follows:

(A) Extraction of animal fat and sebum as raw material (11);

(B) Pre-treatment (12) of the raw material; including high-temperature sterilization and deodorization and removal of impurities;

(C) Raw material mincing (13) by mixing the fat and sebum of the raw material (11);

(D) Fast freezing and sealing (14) of the mixed raw material (11); (E) Heating (15) of the frozen raw material (11);

(F) Mashing (16) of the frozen raw material (11) into sticky and thick gummy matter;

(G) Squeezing and screening (17) of the sticky and thick gummy matter for the release of colloid (18);

(H) Mixing of the released colloid (18) with emulsifying agent (19) allowing the gummy matter (18) transform from greasy substance into watery white wax (10), being the emulsifying agent (19) a product of fatty alcohol and ether sulfate.

Further, thanks to its optimal stability and stickiness, the white wax (10) of this invention is applicable in the making of emulsions and cosmetic liquid as aggregate to cold ironing liquid and rinse agent as well as base for stable emulsification in the making of facial creams, ointment and lipsticks. Being easily mixed with greases used in the making of cosmetic products, the white wax (10) is also applicable as foam stabilizer in the making of shampoo and sprays.

EXAMPLE 1

In an example of the present invention, white wax was manufactured starting with pork skin and pork fat extract, and the finished product was laboratory tested for the analysis of various components. The results of these tests are shown below in Table 1.

TABLE 1

| ITEM | UNITS | RESULT |
| --- | --- | --- |
| Moisture | g/100 g | 39.27 |
| Ash | g/100 g | 0.14 |
| Crude Fat | g/100 g | 52.42 |
| Crude Protein | g/100 g | 7.86 |
| Total Carbohydrate* | g/100 g | 0.31 |
| Mg | ppm | 11.45 |
| Vit A | IU/100 g | 46.28 |
| Niacin | mg/100 g | 0.35 |
| Vit $B_6$ | mg/100 g | 0.01 |
| Vit $B_{12}$ | µg/100 g | 0.39 |

TABLE 1-continued

| ITEM | UNITS | RESULT |
| --- | --- | --- |
| Pantothenic Acid | mg/100 g | 0.09 |
| AV | mgKOH/g | 0.74 |
| POV | mEq/kg | 1.86 |
| BHA | g/kg | |
| BHT | g/kg | 2.13 |
| TBHQ | g/kg | |
| Zn | ppm | 12.62 |
| Cu | ppm | 0.15 |
| Mn | ppm | 0.18 |
| Aerobic plate count | CFU/g | $1.2 \times 10^2$ |
| Vit E | mg/100 g | 0.22 |
| Calorie | Kcal/100 g | 504.46 |

*Total carbohydrate = 100-(moisture + coarse protein + coarse fat + ash)

The white wax (10) of this invention becomes plastic when heated and turns pasty in water. This suggests that white wax (10) can turn into constant status by adding water. For example, when adding small amount of water, the white wax (10) becomes solid (creamy); when adding more water, the white wax (19) becomes liquid.

The aforementioned white wax (10) is made from extracted animal fat and sebum and contains various nutrients (the test report No. 88-1038 empowered by Food Industry Research & Development Institute). The white wax (10), made of animal fat and sebum, which is similar to human fat and sebum, can be easily absorbed by human, creating successful moistening.

Accordingly, the white wax in reference is not only a non-toxic and non-harmful product, with the wide variety of nutrients it contains; the product is nutritive and moistening.

Accordingly, it is to be understood that the embodiments of the invention herein described are merely illustrative of the application of the principles of the invention. Reference herein to details of the illustrated embodiments is not intended to limit the scope of the claims, which themselves recite those features regarded as essential to the invention.

What is claimed is:

1. A process for making wax, comprising the steps of:
    a) pre-treating raw material of animal fat and sebum;
    b) mincing said pre-treated raw material by mixing the fat and sebum;
    c) fast freezing, sealing and heating of the mixed raw material;
    d) mashing of the frozen raw material into sticky and thick gummy matter;
    e) screening of the sticky and thick gummy matter before releasing colloid;
    f) mixing and neutralization of the released colloid by adding emulsifying agent to transform the greasy colloid into watery white wax.

2. The process of claim 1, wherein the pre-treatment of the raw material includes high-temperature sterilization, deodorization and/or removal of impurities.

3. The process of claim 1, wherein the frozen raw material is mashed and the sticky and thick gummy matter is squeezed and screened before releasing colloid.

4. The process of claim 1, wherein the emulsifying agent is a product of fatty alcohol and ether sulfate.

5. A wax material, produced by the process of claim 1.

6. A wax material, produced by the process of claim 2.

7. A wax material, produced by the process of claim 3.

8. A wax material, produced by the process of claim 4.

* * * * *